Figure 1:
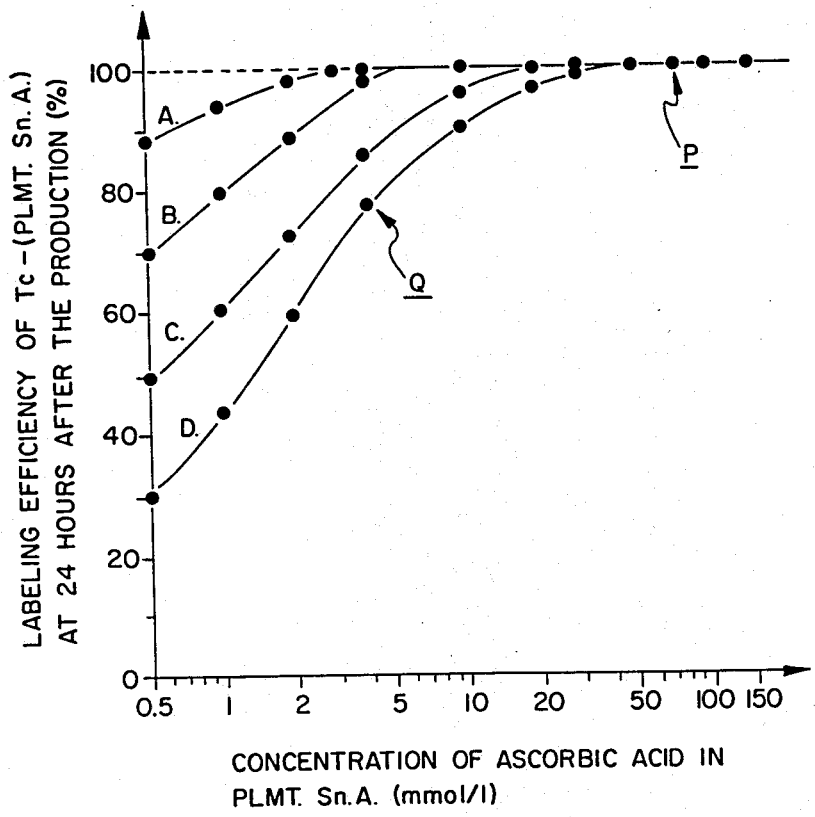

United States Patent [19]

Azuma et al.

[11] Patent Number: 4,489,053
[45] Date of Patent: Dec. 18, 1984

[54] STABLE RADIOACTIVE DIAGNOSTIC AGENT AND A NON-RADIOACTIVE CARRIER THEREFOR

[75] Inventors: Makoto Azuma, Takarazuka; Masaaki Hazue, Amagasaki, both of Japan

[73] Assignee: Nihon Medi-Physics Co., Ltd., Hyogo, Japan

[21] Appl. No.: 446,125

[22] Filed: Dec. 2, 1982

[30] Foreign Application Priority Data

Dec. 3, 1981 [JP] Japan ................................. 56-195215

[51] Int. Cl.³ .................... A61K 43/00; A61K 49/00
[52] U.S. Cl. ............................................ 424/1.1; 424/9
[58] Field of Search ..................................... 424/1.1, 9

[56] References Cited

U.S. PATENT DOCUMENTS

| 3,981,980 | 9/1976 | Baker et al. | 424/1.1 |
|---|---|---|---|
| 4,229,427 | 10/1980 | Whitehouse | 424/1.1 |
| 4,232,000 | 11/1980 | Fawzi | 424/1.1 |
| 4,233,284 | 11/1980 | Fawzi | 424/1.1 |
| 4,247,534 | 1/1981 | Bevan | 424/1.1 |

FOREIGN PATENT DOCUMENTS 6409 2/1982 Japan .................................. 424/1.1

OTHER PUBLICATIONS

Tofe et al., Chemical Abstracts, vol. 93, (1980), #128003r.
Tofe et al., Chemical Abstracts, vol. 85, (1976), #139239h.
Winchell et al., Chemical Abstracts, vol. 91, (1979), #153599f.
Tofe et al., Journal of Nuclear Medicine, vol. 17, No. 9, pp. 820–825, (1976).
Kirk–Othmer Encyclopedia of Chemical Technology, (2nd edition), p. 750, (1963).

Primary Examiner—Christine M. Nucker

[57] ABSTRACT

A stable non-radioactive carrier for use in production of $^{99m}$Tc-labeled radioactive diagnostic agent comprising a chelating agent, a water-soluble reducing agent for pertechnetate and a stabilizer chosen from ascorbic acid and erythorbic acid, and their pharmaceutically acceptable salts and esters in an amount of more than about 100 moles per 1 mol of said water-soluble reducing agent.

4 Claims, 1 Drawing Figure

STABLE RADIOACTIVE DIAGNOSTIC AGENT AND A NON-RADIOACTIVE CARRIER THEREFOR

The present invention relates to a $^{99m}$Tc-labeled radioactive diagnostic agent and a non-radioactive carrier therefor.

Since $^{99m}$Tc has a moderate half life of 6 hours and emits γ-ray of about 140 KeV, it is quite suitable as a nuclide for scintigram imaging. In addition, $^{99m}$Tc can be used as occasion calls because its generator is widely spread. Based upon these facts, $^{99m}$Tc is widely prevailed as a nulcide useful in nuclear medical diagnosis in the present time.

In order to combine $^{99m}$Tc with a chelating agent, it is necessary to reduce $^{99m}$Tc from the heptavalent state (pertechnetate) which is commercially available to a lower valency state. This reduction is ordinarily carried out with a water-soluble reducing agent such as stannous ion. Thus, there is placed on the market a $^{99m}$Tc-labeled radioactive diagnostic agent using stannous ion as the reducing agent. Also are available in the market various compositions containing chelating agents and stannous salts for preparing $^{99m}$Tc-labeled radioactive diagnostic agents. However, the known radioactive diagnostic agent is disadvantageous in that stannous ion used as the water-soluble reducing agent is easily oxidized by oxygen or an oxidizing agent and hence the reduction potency of the reducing agent is lowered during a period between the production and the usage. In order to remove this disadvantage, it was attempted to maintain the oxygen-free state by replacing the air in the container for the radioactive diagnostic agent with nitrogen gas, but any satisfactory result could not be obtained because complete replacement of the air was difficult. A simple means to solve the problem is to increase the concentration of stannous ion. However, this means is not preferable, because the amount of stannous ion to be administered to the patient is increased and, as the result, the toxicity is liable to onset.

On the other hand, it is known that an oxidative substance is formed by radiolysis of the solvent in the $^{99m}$Tc-containing pertechnetate solution used for the preparation of $^{99m}$Tc-labeled radioactive diagnostic agents. Such oxidative substance consumes the reducing agent such as stannous ion and brings about a $^{99m}$Tc-labeled radioactive diagnostic reagent which contains pertechnetate as an impurity. When the radioactivity of $^{99m}$Tc is high, the formation of the oxidative substance caused by direct or indirect action of the radioactivity can not be neglected and a significant amount of various radioactive radiolysis products are formed. Thus, various inconveniences occur in the diagnosis using the radioactive diagnostic agent.

In order to overcome the said inconveniences, there was proposed a technique that the radioactive diagnostic agent or the composition used for the preparation thereof is stabilized by incorporation of a stabilizer such as ascorbic acid or erythorbic acid therein. This technique is disclosed in Japanese patent Publn. (examined) No. 6409/1982. In this publication, however, it is described that, when the amount of the stabilizer is increased, desirable distribution of the radioactive diagnostic agent in a living body is inhibited by competition of the solubilizer and the chelating agent in the radioactive diagnostic agent labeled with $^{99m}$Tc. This is ascribed to the reaction of the stabilizer such as ascorbic acid and $^{99m}$Tc to form a coordination compound, which accumulates in a kidney being not to be diagnosed. This publication, therefore, teaches that the amount of the stabilizer should be less than 100 mols per 1 mol of the reducing agent. However, the $^{99m}$Tc-labeled radioactive diagnostic agent to be placed on the market should contain the radioactivity of about ten times that to be administered to a patient taking the loss of radioactivity during the transportation into consideration. The radiolysis is promoted by the increase in radioactivity and also the vibration during transportation. In these cases, the addition of the stabilizer in the amount less than 100 mols per 1 mol of the reducing agent can not bring about a satisfactory result.

As a result of the extensive study, it has now been found that a stable $^{99m}$Tc-labeled radioactive diagnostic agent and a stable carrier composition for the $^{99m}$Tc-labeled radioactive diagnostic agent can be provided according to the technique described below.

More particularly, it has been surprisingly found that a $^{99m}$Tc-labeled radioactive diagnostic agent, which is stable enough at a high concentration of radioactivity under vibration during the transportation and substantially free from any coordination compound of the stabilizer and $^{99m}$Tc, can be obtained by incorporating therein at least one chosen ascorbic acid and erythorbic acid, and their pharmaceutically acceptable salts and esters in an amount of not less than about 100 mols per 1 mol of the water-soluble reducing agent.

Accordingly, the present invention can be applied to the stabilization of a $^{99m}$Tc-labeled radioactive diagnostic agent or carrier therefor which contains a chelating agent and a water-soluble reducing agent.

According to this invention, there is provided a stable $^{99m}$Tc-labeled radioactive diagnostic agent which comprises a pertechnetate, a chelating agent, a water-soluble reducing agent for the pertechnetate and at least one of ascorbic acid and erythrobic acid, and their pharmaceutically acceptable salts and esters as a stabilizer, the amount of the stabilizer being not less than 100 mols per 1 mol of the water-soluble reducing agent.

There is also provided a stable non-radioactive carrier for a $^{99m}$Tc-labeled radioactive diagnostic agent which comprises a chelating agent, a water-soluble reducing agent for a pertechnetate and at least one of ascorbic acid and erythrobic acid, and their pharmaceutically acceptable salts and esters as a stabilizer, the amount of the stabilizer being not less than 100 mols per 1 mol of the water-soluble reducing agent.

Preparation of the stable $^{99m}$Tc-labeled radioactive diagnostic agent or the stable non-radioactive carrier therefor may be carried out by mixing the essential components as mentioned above in an optional order. For instance, the stable non-radioactive carrier can be produced by incorporating the said stabilizer into a non-radioactive carrier comprising a chelating agent and a water-soluble reducing agent for a pertechnetate. Further, for instance, the stable $^{99m}$Tc-labeled radioactive diagnostic agent can be produced by incorporating the said stabilizer into a $^{99m}$Tc-labeled radioactive diagnostic agent comprising a pertechnetate, a chelating agent and a water-soluble reducing agent for the pertechnetate. Furthermore, for instance, the stable $^{99m}$Tc-labeled radioactive diagnostic agent can be produced by incorporating $^{99m}$Tc-containing pertechnetate into the stable non-radioactive carrier.

The amount of the stabilizer has no upper limit but it should be less than that showing any material toxicity.

The $^{99m}$Tc-labeled radioactive diagnostic agent or the non-radioactive carrier therefor may be formulated in a lyophilized composition, a simple powdery composition, an aqueous solution or the like. In addition to the said essential components, it may contain any conventional additive such as a pH-adjusting agent, an isotonizing agent (e.g. sodium chloride) and a preservative (e.g. benzyl alcohol).

The chelating agent may include N-pyridoxyl-α-amino acid of the formula:

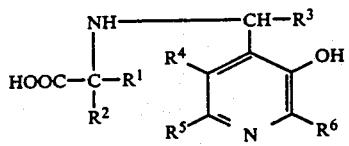

wherein $R^1$ and $R^2$ are each an atom or an atomic group bonded to the α-carbon atom of the α-amino acid and $R^3$, $R^4$, $R^5$ and $R^6$ are each a hydrogen atom, a halogen atom (e.g. chlorine, bromine, iodine, fluorine), a $C_1$–$C_{10}$ alkyl group (e.g. methyl, ethyl, propyl, isopropyl, butyl, pentyl, octyl) or a $C_1$–$C_{10}$ alkyl group substituted with at least one hydrophilic group, or its salt.

Among the said symbols, $R^1$ and $R^2$ can each represent any atom or atomic group which may be present in the α-amino acid of the formula: $H_2N$—$C(R^1)(R^2)$—$COOH$. Examples of such atom and atomic group are hydrogen, $C_1$–$C_{10}$ alkyl, $C_1$–$C_{10}$ alkyl substituted with at least one of amino, imino, nitro, hydroxy, mercapto, $C_1$–$C_{10}$ alkoxy, $C_1$–$C_{10}$ alkylthio, carboxy, oxo, thio, carbamoyl, phenyl, hydroxyphenyl, etc. Thus, said atom or atomic group may be any one which is present in alanine, arginine, asparagine, aspartic acid, cysteine, cystine, glutamine, glutamic acid, glycine, histidine, hydroxylysine, hydroxyproline, isoleucine, leucine, lysine, methionine, norleucine, norvaline, ornitine, phenylalanine, proline, serine, taurine, threonine, tryptophan, tyrosine, valine, etc. The hydrophilic group which may be present on the alkyl group represented by $R^3$, $R^4$, $R^5$ or $R^6$ may include —$SO_3H$, —$SO_3M$, —$O$-$SO_3H$, —$OSO_3M$, —$COOH$, —$COOM$, —$NH_2$, —$N(R_3)X$, —$CN$, —$OH$, —$NHCONH_2$, —$(OCH_2CH_2)_n$—, etc. (wherein M is an alkali metal or an ammonium group, X is an acid residue such as halide, R is a $C_1$–$C_{10}$ alkyl group and n is an optional integer). Other conventional chelating agents such as 3-oxobutyralcarboxylic acid bis(4-methylthiosemicarbazone) are also usable.

The water-soluble reducing agent may be any conventional and pharmaceutically acceptable reducing agent, preferably a stannous salt. The stannous salt is a salt formed from divalent tin and an anion including halide ion (e.g. chloride ion, fluoride ion), sulfate ion, nitrate ion, acetate ion, citrate ion and tartrate ion.

The pharmaceutically acceptalbe salts of ascorbic or erythorbic acid may include the alkali metal salt such as sodium salt and potassium salt. The ester of ascorbic or erythorbic acid may include the $C_1$–$C_{10}$ alkyl ester (e.g. methyl ester, ethyl ester, propyl ester, isopropyl ester, pentyl ester, octyl ester).

Practical and presently preferred embodiments of the invention are illustratively shown in the following Examples.

EXAMPLE 1

Production of a stable non-radioactive carrier for use in the production of a $^{99m}$Tc-labeled radioactive diagnostic agent using N-pyridoxyl-DL-5-methyltryptophan, stannous chloride and ascorbic acid as a stabilizer (hereinafter referred to as "PLMT.Sn.A."):

Dissolved oxygen was removed from sterile and pyrogen-free water by bubbling sterile nitrogen gas. All the following treatments were carried out under aseptic conditions in nitrogen stream. L-(+)-ascorbic acid was dissolved in the deoxygenated water (1000 ml). To the solution was suspended powdery N-pyridoxyl-DL-5-methyltryptophan (2113 mg; prepared according to Heyl et al., J. Am. Chem. Soc., 70, 3429–3431 (1948), hereinafter referred to as "PLMT"). Then, anhydrous stannous chloride (94.8 mg) was added to the suspension.

A 4N aqueous sodium hydroxide solution was gradually dropped to the suspension stirred with a magnetic stirrer to dissolve the powders and adjusted pH to 10.0 giving PLMT.Sn.A. The PLMT.Sn.A. was passed through a filter having opening diameter of 0.22 μm and filled in a vial, the air in which was replaced beforehand by nitrogen gas. By varying the amount of L-(+)-ascorbic acid, a number of PLMT.Sn.A. containing L-(+)-ascorbic acid in various concentrations were produced. The obtained PLMT.Sn.A. was a colorless, clear solution.

EXAMPLE 2

Production of a stable $^{99m}$Tc-labeled radioactive diagnostic agent formed by contacting PLMT.Sn.A. with $^{99m}$Tc-containing pertechnetate (hereinafter referred to as "Tc-(PLMT.Sn.A.)"):

A physiological saline solution (1.0 ml) containing $^{99m}$Tc in the form of sodium pertechnetate was mixed with PLMT.Sn.A. (1.0 ml) obtained in Example 1 in a vial, the air in which was replaced by nitrogen gas. The mixture was stirred sufficiently, heated in a boiling water bath for 15 minutes and cooled to room temperature to give Tc-(PLMT.Sn.A.) as a colorless or pale yellow clear solution. Using physiological saline solutions of various radioactivity concentrations, a variety of Tc-(PLMT.Sn.A.) were obtained.

EXAMPLE 3

Influence of concentrations of ascorbic acid and $^{99m}$Tc-radioactivity on stability of Tc-(PLMT.Sn.A.) (evaluation by TLC):

Stability of Tc-(PLMT.Sn.A.) obtained in Example 2 was evaluated by determining the labeling efficiency on a thin layer plate, after storing in the dark for 24 hours. Thin layer chromatography (TLC) was carried out using a silica gel plate of 0.25 mm in thickness as a stationary phase and a mixture of methylethylketone, methanol and 2M aqueous potassium chloride solution in a volume ratio of 10:9:1 as a mobile phase, developing for about 10 cm and scanning with a radiochromatoscanner. In this chromatography system, Tc-(PLMT.Sn.A.) had a sensitive single peak at an Rf value of about 0.65 and sodium pertechnetate had an Rf value of 0.98. The $^{99m}$Tc-tin colloid and insoluble inorganic technetium chemical species (e.g. $TcO_2$) produced by reduction and hydrolysis remained unmoved at the starting point. The radiolysis product of Tc-(PLMT.Sn.A.) was observed as a wide peak at an Rf value of 0.1–0.4. Accordingly, the labeling efficiency is given by the following equation:

Labeling efficiency (%) =

$$\frac{\text{Radioactivity at } Rf = 0.7}{\text{Total radioactivity on } TLC \text{ plate}} \times 100$$

The relationship between the labeling efficiency after the lapse of 24 hours and the concentrations of ascorbic acid and $^{99m}$Tc-radioactivity at the time of production of the physiological saline solution containing $^{99m}$Tc-containing sodium pertechnetate is shown in FIG. 1 of the accompanying drawing. The concentrations of PLMT and stannous chloride were fixed at 2.113 mg/ml (5.72 mmol/l) and 0.0948 mg/ml (0.5 mmol/l), respectively, as described in Example 1.

It can be clearly seen from FIG. 1 that, when the concentration of radioactivity in the $^{99m}$Tc-containing sodium pertechnetate solution used for Tc-(PLMT.Sn.A.) is 10 mCi/ml (Curve A), the labeling efficiency of 100 % is maintained 24 hours after the production as long as the concentration of ascorbic acid is more than 3 mmol/l. However, the concentration of ascorbic acid is required to be higher in order to maintain the labeling efficiency of 100 % as the concentration of radioactivity increases. On the other hand, it is necessary to use a pertechnetate solution having a concentration of 80–120 mCi/ml at the time of production in order to secure the radioactivity level required to give sufficient informations, taking into consideration the time for transportation, which is about 21 hours at the maximum. Curve D in FIG. 1 shows that, when a sodium pertechnetate solution containing radioactivity of 130 mCi/ml is used, PLMT.Sn.A. must contain ascorbic acid in a concentration of more than 590 mmol/ml in order to maintain the labeling efficiency of 100 %. Considering the safety factor, PLMT.Sn.A. containing 70–80 mmol/ml of ascorbic acid is appropriate for production of Tc-(PLMT.Sn.A.) with 130 mCi/ml, which is possible to maintain the labeling efficiency of 100 %.

In this case, the ratio in molar concentration of ascorbic acid (70–80 mmol/ml) and stannous chloride (0.5 mmol/l) is 140–160. As is evident from FIG. 1, stabilization can also be attained at the concentration of ascorbic acid more than 150 mmol/l, i.e. at the molar concentration ratio (ascorbic acid/stannous chloride) of more than 300.

EXAMPLE 4

Influence of concentrations of ascorbic acid and $^{99m}$Tc-radioactivity on stability of Tc-(PLMT.Sn.A.) (evaluation using laboratory animals):

Animal experiment was conducted to confirm the conditions for stabilization of the diagnostic agent by ascorbic acid. Two kinds of PLMT.Sn.A. containing 75 mmol/l and 4 mmol/l of ascorbic acid, respectively, were produced according to Example 1. Two kinds of Tc-(PLMT.Sn.A.) were produced from the two kinds of PLMT.Sn.A. mentioned above and a $^{99m}$Tc-containing 130 mCi/ml sodium pertechnetate solution, and stored in the dark at room temperature for 24 hours. Then, the labeling ratios of these two Tc-(PLMT.Sn.A.) were determined according to the method as described in Example 3 giving 100 % and 78 %, respectively, as shown by P and Q in FIG. 1. Each 0.2 ml of the two Tc-(PLMT.Sn.A.) was administered intravenously into tail vein of female rats of Spraque-Dawley strain, which were anatomized after an hour and radioactivities in each organ were measured. The results are shown in Table 1.

Since Tc-(PLMT.Sn.A.) is a diagnostic agent adapted for dynamic functional study of hepato-bile duct system, it is desirable that the major part of radioactivity is distributed in small intestine at 1 hour after the administration and is not distributed in other organs, blood or carcass. From this aspect, Tc-(PLMT.Sn.A.) using PLMT.Sn.A. which contains 75 mmol/l of ascorbic acid and having a labeling efficiency of 100 % showed an excellent internal distribution for use as hepato-bile duct imaging agent as seen from Table 1, while in Tc-(PLMT.Sn.A.) using PLMT.Sn.A which contains 4 mmol/l of ascorbic acid and having a labeling efficiency of 78 %, there observed in small intestine 82.12 % of the radioactivity, which is about 11 % lower than that (93.44 %) of the aforementioned Tc-(PLMT.Sn.A.), and also observed relatively high distribution in other organs, blood and carcass. Thus, it was confirmed from the results in Table 1 that the result of the animal experiment is parallel to that obtained in Example 3 and shown in FIG. 1.

TABLE 1

Internal distribution of Tc-(PLMT. Sn. A.) in rat (% to radioactivity administered, at 1 hour after the administration, average for 5 animals)

| Organ | Concentration of ascorbic acid in PLMT. Sn. A. used | |
|---|---|---|
| | 75 mmol/l | 4 mmol/l |
| | Labeling efficiency at the time of administration | |
| | 100% | 78% |
| Liver | 1.32 | 3.92 |
| Small intestine | 93.44 | 82.12 |
| Stomach | 0.04 | 0.10 |
| Kidney | 0.25 | 1.32 |
| Blood (1 ml)* | 0.02 | 0.04 |
| Carcass | 2.18 | 4.22 |
| Bladder (urine) | 2.00 | 7.04 |

Note
*A value when the body weight was normalized to 200 g.

EXAMPLE 5

Toxicity of PLMT.Sn.A. containing 75 mmol/l of ascorbic acid:

The solution of PLMT.Sn.A. containing 75 mmol/l of ascorbic acid obtained in Example 1 was administered intravenously to groups of male SD strain rats, groups of female SD strain rats, each group consisting of 10 animals, at a dose of 1 ml per 100 g of body weight (which dose corresponds to 600 times the normal dose to human beings), and also to groups of male ICR strain rats, groups of femal ICR strain rats, each group consisting of 10 animals, at a dose of 0.5 ml per 10 g of body weight (which dose corresponds to 3000 times the normal dose to human beings). Separately, the same volume of physiological saline solution as above was administered intravenously to groups of animals with the same constitution as above for control. The animals were fed for 10 days and body weight was recorded every day. However, no significant difference was observed in body weight between the medicated and control groups. Then, all the animals were anatomized and inspected for abnormality in various organs. However, no abnormality was observed in any of the organs.

From the above result, it can be safely said that the toxicity of the non-radioactive carrier according to the invention is extremely low.

We claim:

1. A stable non-radioactive carrier for use in production of $^{99m}$Tc-labeled radioactive diagnostic agent comprising a chelating agent, a water-soluble reducing agent for pertechnetate and a stabilizer chosen from ascorbic acid and erythorbic acid, and their pharmaceutically acceptable salts and esters in an amount of more than about 100 moles per 1 mol of said water-soluble reducing agent and in an amount less than that showing any material toxicity, said chelating agent comprising N-pyridoxyl-α-amino acid of the formula

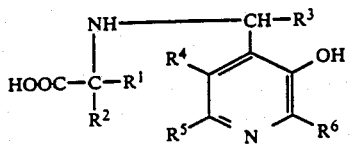

wherein $R^1$ and $R^2$ are each an atom or an atomic group which can be present in α-amino acid of the formula

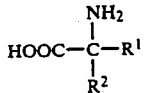

and $R^3$, $R^4$, $R^5$ and $R^6$ are each a hydrogen atom, a halogen atom, a $C_1$–$C_{10}$ alkyl group or a $C_1$–$C_{10}$ alkyl group substituted with at least one hydrophilic group, or its salt.

2. The stable non-radioactive carrier according to claim 1, wherein the water-soluble reducing agent is a stannous salt.

3. A stable $^{99m}$Tc-labeled radioactive diagnostic agent which is produced by contacting $^{99m}$Tc-containing pertechnetate with a non-radioactive carrier comprising a chelating agent, a water-soluble reducing agent for pertechnetate and a stabilizer chosen from ascorbic acid and erythorbic acid, and pharmaceutically acceptable salts and esters in an amount of more than about 100 moles per 1 mol of said water-soluble reducing agent and in an amount less than that showing any material toxicity, said chelating agent comprising N-pyridoxyl-α-amino acid of the formula

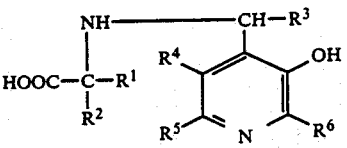

wherein $R^1$ and $R^2$ are each an atom or an atomic group which can be present in α-amino acid of the formula

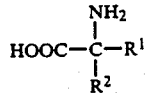

and $R^3$, $R^4$, $R^5$ and $R^6$ are each a hydrogen atom, a halogen atom, a $C_1$–$C_{10}$ alkyl group or a $C_1$–$C_{10}$ alkyl group substituted with at least one hydrophilic group, or its salt.

4. The stable $^{99m}$Tc-labeled radioactive diagnostic agent according to claim 3, wherein the water-soluble reducing agent is a stannous salt.